United States Patent [19]
Benson et al.

[11] Patent Number: 5,876,970
[45] Date of Patent: Mar. 2, 1999

[54] SURFACTANT COMPOSITIONS AND METHODS

[75] Inventors: Bradley J. Benson, Chapel Hill, N.C.; John H. Frenz, Brisbane, Calif.; Cynthia P. Quan, Redwood City, Calif.; Steven Shak, Burlingame, Calif.; Kathleen A. Shiffer, Tiburon, Calif.; Michael C. Venuti, San Francisco, Calif.; John T. Stults, San Mateo, Calif.; David Lesikar, Palo Alto, Calif.

[73] Assignee: Byk Gulden Lomberg Chemische Fabrik GmbH, Constance, Germany

[21] Appl. No.: 278,189

[22] Filed: Jul. 21, 1994

Related U.S. Application Data

[63] Continuation of Ser. No. 89,411, Jul. 9, 1993, abandoned, which is a continuation of Ser. No. 550,601, Jul. 10, 1990, abandoned, which is a continuation-in-part of Ser. No. 378,688, Jul. 11, 1989, abandoned.

[51] Int. Cl.⁶ .......................... C12P 21/02; C07K 14/47; C07H 21/04
[52] U.S. Cl. ........................ 435/69.1; 530/350; 536/23.5
[58] Field of Search .............................. 435/69.1; 436/71, 436/86, 161, 183; 530/350; 536/22.1, 23.1, 23.5

[56] References Cited

U.S. PATENT DOCUMENTS 5,223,481  6/1993  Curstedt et al. ............................ 514/12

FOREIGN PATENT DOCUMENTS 0 172 007  2/1986  European Pat. Off. .
0 368 823  5/1990  European Pat. Off. .
WO 89/04326  5/1989  WIPO .

OTHER PUBLICATIONS

Alberts, B. et al. Molecular Biology of the Cell, Second Edition. New York: Garland Publishing, Inc. 1989, p. 265.

O'Brien, P.J. et al. "Acylation of disc membrane rhodopsin may be nonenzymatic" Journal of Biological Chemistry (Apr.1987), vol. 262, No. 11, pp. 5210–5215.

Johansson et al., "Size structure of the hydrophobic low molecular weight surfactant–associated polypeptide" Biochemistry(1988) 27:3544–3547.

Whitsett et al., "Immunologic identification of a pulmonary surfactant–associated protein of molecular weight =6000 daltons" Chem. Abstracts(1986) 105:407 (abstract No. 94932s).

Fujiwara et al., "Pulmonary surfactant phospholipids from turkey lung: comparison with rabbit lung" Am. J. Physiol. (1970) 218(1):218–225.

Merritt et al., "Prophylactic treatment of very premature infants with human surfactant" N. Engl. J. Med. (1986) 315(13):785–790.

Klaus et al., "Composition of surface–active material isolated from beef lung" Proc. Natl. Acad. Sci. USA (1961) 97:1858–1859.

Avery et al., "Surface properties in relation to atelectasis and hyaline membrane disease" Am. J. Dis. Child (1959) 97:517–523.

Halliday et al., "Controlled trial of artificial surfactant to prevent respiratory distress syndrome" Lancet (1984) 1:476–478.

Enhorning et al., "Prevention of neonatal respiratory distress syndrome by tracheal instillation of surfactant: a randomized clinical trial" Pediatrics (1985) 76:145–153.

Kwong et al., "Double–blind clinical trial of calf lung surfactant extract for the prevention of hyaline membrane disease in extremely premature infants" Pediatrics (1985) 764:585–592.

Jobe et al., "Surfactant treatment: experimental basis for clinical use" Am. Rev. Resp. Dis. (1987) 136:1032–1033.

Glasser et al. "Two SP–C genes encoding human pulmonary surfactant proteolipid" J. Biol. Chem. (1988) 262(21):10326–10331.

Revak et al., "Use of human surfactant low molecular weight apoproteins in the reconstitution of surfactant biologic activity" J. Clin. Invest. (1988) 81:826–833.

Glasser et al., "cDNA and deduced amino acid sequence of human pulmonary surfactant–associated proteolipid SPL-(Phe)" Proc. Natl. Acad. Sci. USA (1987) 84:4007–4011.

Jacobs et al., "Isolation of a cDNA clone encoding a high molecular weight precursor to a 6–kDa pulmonary surfactant–associated protein" J. Biol. Chem. (1987) 262(20):9808–9811.

Floros et al., "Isolation and characterization of cDNA clones for the 35–kDa pulmonary surfactant–associated protein" J. Biol. Chem. (1986) 261(19):9029–9033.

White et al., "Isolation and characterization of the human pulmonary surfactant apoprotein gene" Nature (1985) 317:361–363.

Whitsett et al., "Characteristics of human surfactant–associated glyoproteins A" Pediatr. Res. (1985) 19(5):501–508.

Warr et al., "Low molecular weight human pulmonary surfactant protein (SP5): isolation, characterization, and cDNA and amino acid sequences" Proc. Natl. Acad. Sci. USA (1987) 84:7915–7919.

Hawgood et al., "Nucleotide and amino acid sequences of pulmonary surfactant protein SP 18 and evidence for coperation between SP 18 and SP 28–36 in surfactant lipid adsorption" Proc. Natl. Acad. Sci. USA (1987) 84:66–70.

Glasser et al., "cDNA, deduced polypeptide structure and chromosomal assignment of human pulmonary surfactant proteolipid, SPL(pVal)" J. Biol. Chem. (1988) 263(1):9–12.

(List continued on next page.)

Primary Examiner—Dian C. Jacobson
Assistant Examiner—Kawai Lou
Attorney, Agent, or Firm—Morrison & Foerster LLP; Tyler M. Dylan, Ph.D.

[57] ABSTRACT

Stable lung surfactant compositions are provided, as well as methods for their preparation, modification, formulation, assay, and therapeutic use.

6 Claims, 1 Drawing Sheet

OTHER PUBLICATIONS

Curstedt et al., "Hydrophobic surfactant–associated polypeptides: SP–C is a lipopeptide with two palmitolated cysteine residues, whereas SP–B lacks covalently linked fatty acyl groups" *Proc. Natl. Acad. Sci. USA* (1990) 87:2985–2989.

Kuroki et al., "Chemical modification of surfactant protein a alters high affinity binding to rat alveolar type II cells and regulation of phospholipid secretion" *J. Biol. Chem.* (1988) 263(33):17596–17602.

Kuroki et al., "Chemical modification of surfactant protein A alters high affinity binding to rat alveolar type II cells and regulation of phospholipid secretion" *Chemical Abstracts* (1988). 109(21):477 abstract No. 187827j.

Bizzozero et al., "Autoacylation of myelin proteolipid protein with acyl coenzyme A" *J. Biol. Chem.* (1987) 262(28):13550–13557.

Buehler et al., *Survey of Organic Syntheses* (Wiley–Interscience, 1970), pp. 807–809.

Musbek et al., "Glycoprotein Ib and glycoprotein IX in human platelets are acylated with palmitic acid through thioester linkages" *J. Biol. Chem.* (1989) 264(17):9716–9719.

Schultz et al., "Fatty acylation of proteins" *Ann. Rev. Cell Biol.* (1988) 4:611–647.

Cronan et al., "Chemical synthesis of acyl thioester of acyl carrier protein with native structure" *Proc. Natl. Acad. Sci. USA* (1981) 78(9):5440–5444.

Mack et al., "Cell–free fatty acylation of microsomal integrated and detergent–solubilized glycoprotein of vesicular stomatitis virus" *J. Biol. Chem.* (1987) 262(9):4297–4302.

Noren et al., "A general method for site–specific incorporation of unnatural amino acids into proteins" *Science* (1989) 244:182–187.

Stuart & Young, *Solid Phase Peptide Synthesis* (Pierce Chemical Co., 1984), 2nd ed., pp. 103–107, 118–122.

Tomich et al., "Prevention of aggregation of synthetic membrane–spanning peptides by addition of detergent" *Analytical Biochemistry* (1988) 174:197–203.

El Rassi, Ziad, "High performance liquid chromatography of membrane proteins" *Biochromatography* (1988) 3:188–199.

Johansson et al., "Hydrophobic 3.7 kDa surfactant polypeptide: structural characterization of the human and bovine forms" *FEBS Letters* (1988) 232(1):61–64.

Tanaka et al., "Lung surfactants II. Effects of fatty acids, triacylglycerols and protein on the activity of lung surfactant" *Chem. Pharm. Bull.* (1983) 31(11):4100–4109.

Chung et al., "Effect of surfactant–associated protein–A (SP–A) on the activity of lipid extract surfactant" *Biochim. Biophys. Acta* (1989) 1002:348–358.

Takei et al., "Synthetic surfactants for the treatment of apneumatosis" *Chemical Abstracts* (1986) 105(8):379 abstract No. 66463w.

Whitsett et al., "Differential effects of epidermal growth factor and transforming growth factor–β on synthesis of $M_r$= 35,000 surfactant–associated protein in fetal lung" *J. Biol. Chem.* (1987) 262(16):7908–7913.

Hamosh et al., *Chemical Abstracts* (1981) 95 abstract No. 58927k.

Brown et al., *CPC Critical Reviews in Clinical Laboratory Sciences* (1982), pp. 85–159.

SURFACTANT COMPOSITIONS AND METHODS

This is a continuation of application Ser. No. 08/089,411 filed on Jul. 9, 1993, now abandoned, which is a continuation of application Ser. No. 07/550,601 filed on Jul. 10, 1990, now abandoned, which is a continuation-in-part of application Ser. No. 07/378,688 filed Jul. 11, 1989, now abandoned.

BACKGROUND OF THE INVENTION

This invention relates to lung surfactants, stable surfactant protein compositions and formulations, and methods for the preparation and assay thereof.

Respiratory distress syndrome (RDS), also known as hyaline membrane disease, is a major cause of morbidity and mortality of the prematurely born infant. RDS is believed to be caused primarily by a deficiency of lung surfactant—a lipid-protein mixture which coats the airspaces of the lung—thereby reducing the surface tension and preventing airspace collapse. The principal component of lung surfactant—dipalmitoylphosphatidylcholine (DPPC)—was identified several years ago (Klaus, et al., Proc. Natl. Acad. Sci. USA 47:1858, 1961; Avery, et al., Am. J. Dis. Child. 97:517, 1959). It is believed that administration of lung surfactant to an individual having or at risk of developing RDS is a desirable therapy, and the literature discloses various clinical studies of therapeutic administration of different lung surfactant preparations.

The literature contains various lung surfactant protein preparations, including those with DPPC. Generally, preparations can be classified into five types. These include 1) natural human surfactant (purified from human amniotic fluid), (Merritt, et al., N. Engl. J. Med. 315:787, 1986,), 2) semisynthetic surfactant (prepared by combining DPPC and high density lipoprotein), (Halliday, et al., Lancet 1:476, 1984), 3) animal lung surfactant (isolated by organic extraction of the whole lung or lavage fluid), (Fujiwara, supra; Enhorning, et al., Pediatrics 76:145, 1985; Kwong, et al., Pediatrics 76:585, 1985), and 4) purified human surfactant apoproteins (SP-A, SP-B, and/or SP-C purified from natural sources or derived by recombinant DNA technology; see Jobe et al., Am. Rev. Resp. Dis. 136:1032, 1987, and Glasser et al., J. Biol. Chem. 263:10326, 1988) which are reconstituted with surfactant lipids (Revak, et al., J. Clin. Invest. 81:826, 1987).

It has been observed that lung surfactant protein tends to aggregate over time. It is therefore an object of this invention to provide more stable lung surfactant protein compositions and formulations, and methods for making same. It is a further object of this invention to provide lung surfactant protein compositions and formulations with improved biological properties and therapeutic efficacy.

It is also believed desirable for certain therapeutic uses that the surfactant administered have substantially the same structure as natural mammalian surfactant. It is therefore an additional object of this invention to provide lung surfactant protein similar in structure to naturally occurring surfactants.

SUMMARY OF THE INVENTION

In the course of their work with lung surfactant, the inventors have discovered that at least some of the cysteine residues present in lung surfactant protein are esterified to fatty acids in the natural composition, and that this results in reduced aggregation and a more stable formulation.

Accordingly, in one embodiment, methods are provided comprising the modification of the cysteine residues of mammalian (natural or recombinant) lung surfactant protein. Preferred modifications reduce the tendency to aggregation observed of surfactant. These modifications are preferably but not necessarily covalent, and proceed by chemical or enzymatic methods.

Preferred embodiments involve the modification of surfactant protein cysteine residues having free sulfhydryl groups. Surfactant protein is modified with fatty acids or other chemical groups. This modification may proceed so that the cysteine residue is incapable of forming disulfide bonds. In some embodiments, activated derivatives of fatty acids capable of reacting with sulfhydryl groups are reacted with lung surfactant protein having free sulfhydryl groups at the cysteine residues. The resultant reaction product comprises lung surfactant protein containing fatty acid ester groups at its cysteine residues.

In one embodiment, an activated derivative of palmitic acid is used to esterify lung surfactant protein having free sulfhydryl groups at its cysteine residues by reacting the lung surfactant protein with a 4 to 500-molar excess of palmitoyl chloride, preferably a 100 to 400-molar excess of palmitoyl chloride. The reaction is preferably carried out in aprotic solvent to minimize side reactions. The solvents may preferably be mixtures of tetrahydrofuran (THF) and dimethylformamide (DMF) containing one or more acids to lower the pH. A preferred solvent mixture comprised a 50:50 v/v mixture of THF and DMF with 0.1% acid, preferably trifluoroacetic acid. Other acids, such as acetic, phosphoric, or hydrochloric acid may also be employed in the reaction mixture.

In another embodiment, surfactant protein is modified through incubation with a crude extract of lung tissue, or extracts of lung cells such as Type II lung cells or Clara cells under suitable conditions and for a sufficient length of time to palmitoylate cysteine residues in the surfactant protein.

In other embodiments, surfactant protein is analyzed to determine if cysteine residues have been modified. To this end, methods are provided for the mass spectrographic analysis of surfactant protein. In another embodiment, reverse-phase HPLC is provided, utilizing a preferred solvent system of water, butanol, and trifluoroacetic acid (TFA). In yet another embodiment, surfactant protein is analyzed by thin layer chromatography, utilizing a preferred solvent system of butanol, glacial acetic acid, and water. Surfactant protein may also be analyzed by nuclear magnetic resonance.

Still other objects are accomplished through the provision of stable surfactant formulations. Preferred embodiments of such formulations include formulations comprising surfactant protein and reducing agents such as N-acetyl cysteine. In other embodiments, additional reagents (e.g. other reducing agents or antioxidants) which inhibit disulfide bond formation are included in the formulation.

Surfactant protein modified according to the teachings of this invention may be useful in the prevention and treatment of respiratory distress syndrome. In one embodiment, pharmaceutical preparations are provided which are suitable for administration to mammalian adults or infants having or at risk of developing respiratory distress syndrome, as well as to individuals at risk before their first breath.

DETAILED DESCRIPTION OF THE INVENTION

Figure 1C:
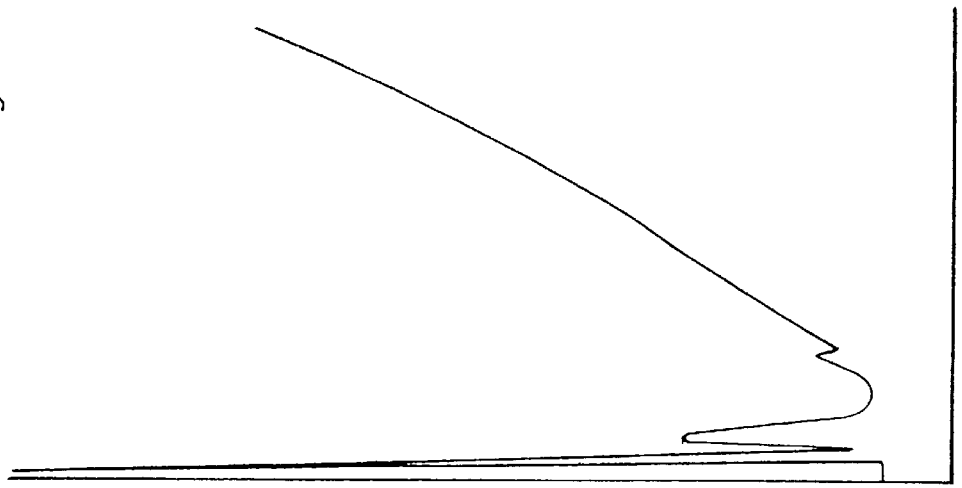
FIG. 1 shows the analysis of HPLC analysis of palmitoylated recombinant SP-G.

Surfactant protein as defined herein means any protein which, when mixed with appropriate lipids, is capable of lowering the surface tension at air-liquid interfaces in the lung. This definition encompasses lung surfactant protein, as described above, together with its amino acid, glycosylation and other variants or derivatives. The literature discussed supra describes suitable lung surfactant proteins. It is expected that other surfactant protein variants and derivatives will become available in the future, and these are to be considered to fall within the scope of this invention.

Lung surfactant may be prepared by known methods from synthetic dipalmitoylphosphatidylcholine (DPPC), egg or synthetic phosphatidylglycerol (PG), and purified surfactant apoproteins (SP-B and/or SP-C and/or SP-A). Purified surfactant apoproteins are obtained by recombinant methods or direct synthesis using published nucleotide and amino acid sequences (Glasser, et al., Proc. Natl. Acad. Sci. U.S.A. 84:4007, 1987; Jacobs, et al., J. Biol. Chem. 262:9808, 1987; Floros, et al., J. Biol. Chem. 261:9029, 1986; White, et al., Nature 317:361, 1985; Whitsett, et al., Pediatr. Res. 19:501, 1985; Warr, et al., Proc. Natl. Acad. Sci. U.S.A. 84:7915, 1987; Hawgood, et al., Proc. Natl. Acad. Sci. U.S.A. 84:66, 1987; Glasser, et al., J. Biol. Chem. 263:9, 1988, Glasser, et al., supra, J. Biol. Chem. 263:10326, 1988; and Jobe et al., Am. Rev. Resp. Dis. 136:1032, 1987). Desirably, surfactant apoproteins are reconstituted with surfactant lipids, Revak, supra.

Purified surfactant proteins may also be obtained from amniotic fluid, human or animal, or from cell culture, using cells which naturally produce these molecules, such as Type II lung cells or Clara cells. Surfactant protein is also obtained by isolation of natural surfactant from human or animal amniotic fluid. Alternatively, surfactant protein may be isolated by known methods—e.g. by organic extraction of lung tissue or by lavage from human or animal lung, and then supplemented with phospholipids, as desired. Surfactant from other animal species can be used in the treatment of human respiratory distress syndrome, and vice versa.

Fatty acids as used herein refers to non-toxic, straight chain or branched chain compounds, ranging from three to twenty-four carbons; they may be saturated or unsaturated. Suitable fatty acids include, for example, palmitic acid, oleic acid, linoleic acid, and stearic acid.

Several strategies for the modification of surfactant protein are encompassed by this invention, including covalent modification of cysteine residues with fatty acids or other chemical groups.

In some embodiments, mammalian lung surfactant protein cysteine residues are covalently modified with palmitic acid, resulting in a molecule with a structure similar to that of the native surfactant. Such modifications may be chemical, enzymatic, or the result of direct expression of a modified surfactant protein.

For example, surfactant apoprotein may be chemically modified by reaction with palmityl chloride, as described above and in Example 1. Alternatively, surfactant protein may be modified by reaction with palmitoyl CoA (described for application to myelin proteolipid by Bizzozero et al., J. Biol. Chem. 262:13550, 1987). It may also be modified with activated fatty acid esters; particularly preferred are optionally substituted phenyl-esters of palmitic acid such as nitrophenyl esters, where there are no more than five optional substitutions, which may be nitro, methoxy, halogen, or carboxylate. Preferred derivatives also include palmitate esters of 2-hydroxy pyridine, or 4-hydroxy pyridine. Preparation of these activated derivatives are within the ordinary skill of the art, as shown in C.A. Buehler et al., Survey of Organic Syntheses, page 807, Wiley Book Vol.1 (1970). For example, the reagents above are formed by the reaction of palmitoyl chloride with the appropriate hydroxy-benzene or hydroxy-pyridine derivative. Derivatives of other fatty acids may desirably be made by known methods without undue experimentation. See, e.g., Muzbeck et al., Jour. Biol. Chem. 264:9716, 1989, and Schultz et al., Ann. Rev. Cell Biol. 4:611, 1988. The reaction of surfactant protein with activated fatty acids is performed in organic solvents in which both reactants are soluble, at approximately 4°–100° C., for 1–48 hours. Preferably, aprotic organic solvents such as DMF or THF are utilized.

Enzymatic modification of surfactant protein may be accomplished by application of methods known in art. For example, palmitylation or other modifications of surfactant protein may be accomplished by reaction with microsomal membranes from mouse myeloma cell line MPC 11 (Mack et al., J. Biol. Chem. 262:4297, 1987), by reaction with crude cell extracts, membrane extracts or purified protein from other mammalian cells.

In other embodiments, surfactant protein is modified with fatty acids or other chemical groups by a variety of known methods, including but not limited to the following methods: (1) covalent modification using dehydrating or activating agents such as N,N'-dicyclohexylcarbodiimide (DCC) or ethyoxy-ethoxycarbonyl-dihydroquinoline (EEDQ); (2) acylation, using ketenes, anhydrides, isothiocyanates, or beta-lactones; (3) carbamoylation using cyanates; (4) hemimercaptal or hemimercaptol formation using aldehydes and some keto acids; (5) alkylation and arylation, by addition to activated double bonds (using N-ethylmaleimide), by reactions with quinones, by reaction with haloacids and their amides (using iodoacetic acid, or alpha-bromohexadecanoic acid), by methylation reactions (such as with dimethylsulfate), by sulfoalkylation, by arylation (with nitrobenzene compounds), or by reaction with diazo compounds; (6) reaction with metal ions and organic mercury compounds such as mercuric chloride; (7) reaction with arsenic compounds; (8) reaction with sulfites; (9) oxidation reactions; and (10) reaction with sulfenyl halides to form mixed disulfides.

Surfactant protein may be modified within a host cell, or expressed using modified amino-acyl tRNA for site-specific incorporation (see e.g. Noren et al., Science 244:182 (1989)).

This invention also encompasses post-translational modifications to a recombinantly produced protein. It is currently preferred that any post-translational modifications take place within 24, and preferably within a few hours of recovery from a host cell or microorganism. Modifications may also be made to surfactant protein after it is formulated, as will be discussed below. Pharmaceutical compositions comprising surfactant protein modified according to the practice of this invention are encompassed herein, and described in more detail below.

Methods for detecting the presence of modifications to lung surfactant protein are encompassed within the scope of this invention. In one embodiment, the mass spectrum of a sample is obtained and analyzed. Such an embodiment is shown in the examples below.

In other embodiments, thin layer chromatography (TLC) is performed on a sample. While this approach to peptide analysis is common in the field, see e.g. Stuart and Young,

*Solid Phase Peptide Synthesis*, pp 103–107, and 118–122, (Pierce Chem. Co., 2d.ed., 1984), the inventors have discovered an improved method, using a novel solvent system. In a particularly preferred embodiment, 1"×3" Whatman silica gel plates are used. A 20μl isopropanol extract of cells (~0.3 μg/μl) is loaded onto the TLC plates. A preferred solvent system comprising butanol, glacial acetic acid (HOAc), and $H_2O$ is utilized; while relative proportions of this compounds are envisioned it is presently preferred to utilize volume ratios of 4:1:2. One may use a ninhydrin spray for identification of samples, however different commonly used sprays may be desirable to identify samples containing fatty acids.

In another embodiment, surfactant protein is analyzed by reverse phase HPLC; see e.g. Tomich et al., *Analytical Biochemistry* 174:197–203 (1988), Rassi, *BioChromatography* 3:188, 1988, and Johansson et al., *FEBS Letters* vol 232, no. 1, pp61–64 (1988). The inventors have discovered novel solvent systems employing an acid, isopropanol, and water, and for certain conditions optionally employing butanol. In one presently preferred embodiment, a Nucleosil C18 column is used, flow rate of 0.5 ml/min, at a preferred temperature of 25° C. Two mobile phases are used: "A" phase comprised of 1 ml trifluoroacetic acid (TFA) and 1000 ml water, and "B" phase comprised of 1 ml TFA, 950 ml isopropanol, and 50 ml water. A preferred gradient is 58–69% "B" in 22 minutes. Absorbance is measured at 214 nm. In one embodiment, surfactant analyzed by the foregoing method appeared as a peak at approximately 19 minutes. Use of different acids in the place of TFA is envisioned, such as phosphoric or hydrochloric acid, and different volumes and proportions may be used within the scope of this invention.

In another embodiment of the above reverse-phase HPLC process, a Vydac C4 (#7) column is used, flow rate of 0.5 ml/min, at a temperature of approximately 25° C. As above, two mobile phases are used: "A" phase comprised of 1 ml trifluoroacetic acid (TFA), 300 ml isopropanol, and 800ml water, and "B" phase comprised of 1 ml TFA, 300 ml isopropanol, 200 ml water and 600 ml butanol. For these reagents, a preferred gradient is 0–50% "B" in 120 minutes. Absorbance is measured at 228 nm, with surfactant analyzed by the foregoing method appeared as a peak at approximately 64.7 minutes. This particular embodiment may be preferred for the analysis of monomeric surfactant. preferred for the analysis of monomeric surfactant.

Different methods of analysis are envisioned with the practice of this invention. An additional example of an HPLC system is described in the Examples below. Further, surfactant protein may be analyzed by NMR.

Surfactant for therapeutic administration is placed into sterile, isotonic formulations together with any desired cofactors. The formulation of surfactant protein is preferably liquid. While conventional parenteral solutions or buffers are usable, it is presently preferred to formulate surfactant protein with excipients which inhibit disulfide bond formation. In one preferred embodiment, surfactant protein is formulated with DPPC, a negatively charged phospholipid containing an unsaturated fatty acid, and a reducing agent or anti-oxidant. Palmitic acid is also desirable. A presently preferred reducing agent is N-acetyl-L-cysteine, however dithiothreitol (DTT), or any of the following commonly used agents may desirably be utilized: inhibitors of disulfide formation (EDTA, or a vial sealed without oxygen and with a nitrogen headspace), tributylphosphine or other tertiary phosphines, mercaptoethanol, D-cysteine, L-cysteine, glutathione (reduced), lipoic acid, coenzyme A, thioredoxin, acyl-carrier proteins that contain 4'-phosphopantetheine, thioglycolic acid, ethylenediamine, maleic acid, sodium metabisulfite or sodium thiosulfate, monothioglycerol, or antioxidants such as catechols, hydroquinones, BHT, ascorbic acid, vitamin E, and gallates. The final concentration of surfactant protein in solution is typically about 1.0–30 mg phopholipid/ml.

In a preferred embodiment, surfactant is formulated according to the following method. Surfactant apoprotein and a mixture of lipids is dried down from organic solvents (evaporation under nitrogen). Typically, the mixture of lipids includes DPPC, 1-palmitoyl-2-oleoyl-phosphatidylglycerol (POPG), and palmitic acid (PA). The ratio of DPPC to POPG is preferably from 50:50 to 90:10. The ratio of (DPPC+POPG) to surfactant protein is preferably from 50:1 to 5:1. The ratio of PA to (DPPC+POPG) is preferably from 0 to 0.2. Other unsaturated acidic lipids than POPG are suitable. In a particularly preferred embodiment, the ratio of DPPC to POPG to palmitic acid is 7:3:1, and with a final phospholipid concentration of 3 times the amount of lipid. It is further presently preferred to incorporation calcium into the formulation, at approximately 0.01 mg/ml–10 mg/ml $Ca^{++}$ (see Chung et al., Biochimica et Biophysica Acta 1002:348–358 (1989)).

After the addition of a first hydration buffer (such as 20 mM Na Acetate, pH 6.5, or more preferably 20 mM succinate, pH 6.5, which may contain a reducing agent such as DTT or N-acetyl cysteine in a molar ratio to the surfactant protein of from 2:1 to 600:1 or an antioxidant), the mixture is heated at preferably 65° C. for approximately 15 minutes. This dispersion is lyophilized for approximately 12–24 hours. The lyophilized product may be stored at –20° C. The lyophilized dispersion is rehydrated at approximately 37° C. for about 15 minutes, in a second hydration buffer which may be water, in a volume equal to that used for the first hydration buffer. The final concentration of surfactant may be from 1.0–30 mg phospholipid/ml and is preferably at approximately 10 mg/ml. For embodiments using N-acetyl cysteine as the reducing agent, molar ratios of 100–300:1 (with respect to SP-C) are presently preferred, with 150–250:1 particularly preferred. For embodiments using DTT as the reducing agent, ratios of 100:1 are presently preferred.

Surfactant protein may be provided as lyophilized powder for ultimate delivery in solution. Surfactant protein can also be administered from sustained release compositions, for example as polylactide or polyhydroxylbutyrate implants or liposomes such as are described in EP 17,2007A, or by continuous infusion.

Surfactant protein also is suitably formulated with other commonly known pharmacologic agents in order to modify or enhance the half-life, the distribution, or the therapeutic activity of the surfactant. The surfactant protein formulations may contain agents such as unsaturated or saturated fatty acids, and triglycerides previously suggested for use in surfactant dosage forms (Tanaka, et al., *Chem. Pharm. Bull.* 31:4100, 1983).

Surfactant protein optionally is administered together with other agents or therapies heretofore employed in the therapy of respiratory distress syndrome. Therapies or agents which are used optionally in a course of therapy with surfactant include, for example, an interferon (including gamma interferon), corticosteroids, thyroid hormone, tocolytics, relaxin, male and female sex hormones, prolactin, insulin, insulin-like growth factor-1, and growth and/or differentiation factors which could induce differentiation of type II cells in fetal lungs and/or increase their surfactant production, such as epithelial growth factor, transforming growth factor beta, or colony stimulating factors. See, for example, Whitsett, et al., J. Biol. Chem. 262:7908 (1987). Other agents include vitamin E, superoxide dismutase, alpha-1-antitrypsin and other antiproteases, selenium, vitamin A, antibiotics, immunoglobulins, and antiviral agents. These other agents or therapies are used at the same time as surfactant is administered or in a sequential course of therapy.

The therapeutically effective dosage of surfactant protein to be employed generally will range about from about 5–900 mg per administration, although the dose will be dependent upon the properties of the surfactant protein employed, e.g. its activity and biological half-life, the concentration of the surfactant protein in the formulation, the rate of dosage, the clinical tolerance of the patients involved, the pathological condition of the patients and the like, as is well within the skill of the physician. It will be appreciated that the practitioner will adjust the therapeutic dose in line with clinical experience for any given surfactant protein.

Surfactant protein may be delivered to the lungs of the fetus transamniotically, and/or to an infant after birth by conventional direct installation after placement of an endotracheal tube. Surfactant protein may be delivered after birth by aerosol, using alternatively a dry power aerosol, a liquid aerosol generated by ultrasonic or jet nebulization, or a metered dose inhaler, again avoiding the complications of endotracheal tube placement.

It should be understood that the Examples below are for illustrative purposes only, and are not to be construed as limiting this invention in any manner.

EXAMPLES

Example 1
Production of Acylated (Palmitoylated) SP-C Using Palmitoyl Chloride.

Human recombinant SP-C (rSP-C) was produced by expression of an SP-C:chloramphenicol acetyltransferase (CAT) fusion protein in E. coli and purified by known techniques. The expressed protein was packaged intracellularly as insoluble refractile bodies (inclusion bodies). These bodies were separated from soluble proteins by centrifugation after cell disruption. The inclusion bodies were solubilized in guanidine hydrochloride and the fusion protein was cleaved by addition of hydroxylamine. The concentration of guanidine was reduced by dilution allowing precipitation of the "mature" SP-C. The SP-C was extracted with organic solvents (isopropanol, chloroform:methanol, etc.). Final purification was effected by combinations of gel permeation and reverse phase chromatography.

The rSP-C was solubilized in 50/50 volume/volume dimethyl formamide/tetrahydrofuran containing 0.1% trifluoroacetic acid (other solvents such as 1-methyl-2-pyrrolidinone are also useful for the reaction). Palmitoyl chloride was then added at 400-fold molar excess compared to SP-C.

The SP-C:palmitoyl chloride mixture was flushed with nitrogen and heated to 37° C. for 16 hours. At the end of the reaction, the acylated SP-C was separated by reverse phase HPLC according to the following procedures. Sample Prep: A 25 $\mu$l aliquot of the incubation mixture containing 25 $\mu$g SP-C was dried in the speed vac. The dried sample was taken up in 53 $\mu$l of 95% isopropanol in 50 mM HCl and then diluted with 47 $\mu$l of 50 mM Ccl. The final sample was in 100 $\mu$l of 50% isopropanol in 50 mM HCl for injection into HPLC. All samples were incubated overnight at 37° C.

Figure 1B:
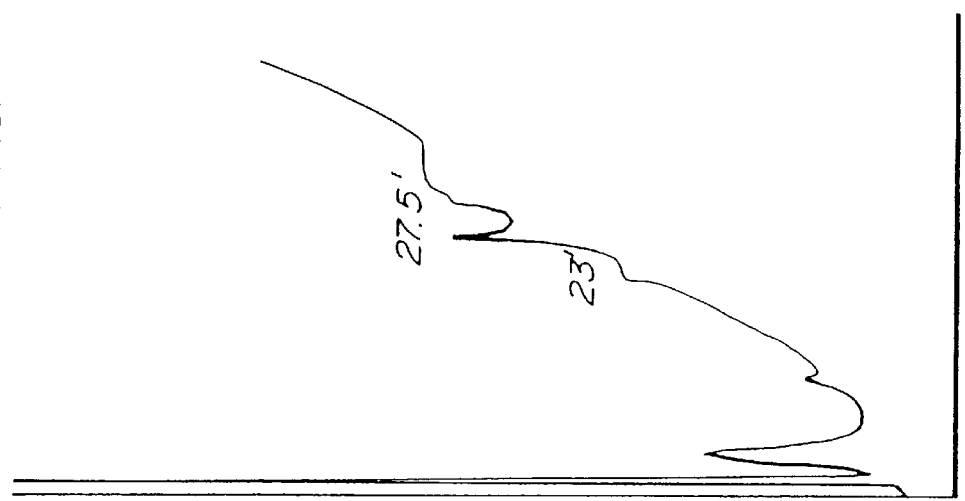
Figure 1A:
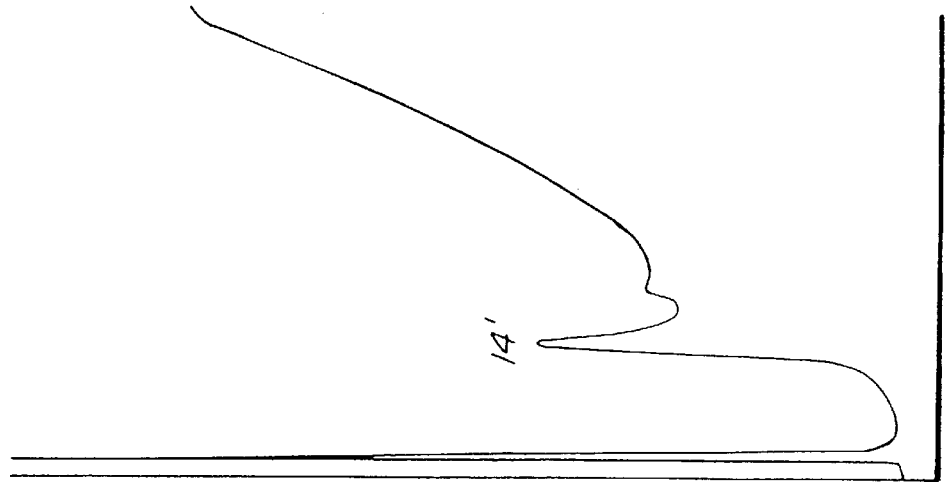

HPLC Column: Reverse phase C8 cartridge (2.1 mm×3 cm)
Gradient: Buffer A: 5 mM HCl Buffer B: 100% isopropanol in 5 mM HCl 35%–95% Buffer B, 40 min linear gradient
Flow rate: 0.5 ml/min
Detection: UV absorbance at 228 nm The HPLC results for the following samples are shown in FIG. 1:
1. Control (rSP-C in DMF/THF/TFA)
2. Palmitylated rSP-C (rSP-C+Palmityl chloride in DMF/THF/TFA)
3. Palmityl Chloride Reagent Blank (Palmityl chloride in DMF/THF/TFA)

The recombinant SP-C control eluted at 14 min. After treatment of rSP-C with palmitoyl chloride, several new peaks appeared in the chromatogram. The major new peak eluted at 27.5 min. This elution position corresponds to a dipalmitoylated SP-C (based on elution position of natural bovine SP-C). There is also a minor new OD peak that eluted at 23 min., which may represent monopalmitoylated SP-C. There are several smaller peaks that elute later than 27.5 min. All of the peaks were collected and run on SDS PACE gels all confirmed to contain SP-C. After treatment with palmitoyl chloride, no SP-C was seen eluting in the position of recombinant SP-C. This indicated that all of the SP-C had reacted with the palmitoyl chloride and was converted to palmitoylated forms. The palmityl chloride reagent blank gave a clean absorbance profile. The peak eluting at 27.5 min. was collected and subjected to mass spectral analysis. The mass obtained was consistent with rSP-C containing two palmitates.

Example 2
Production of Acylated (Palmitoylated) SP-C Using Activated Fatty Acid Esters.

2-(Palmitoyloxy) pyridine hydrochloride was prepared by the reaction of palmitoyl chloride with 2-hydroxypyridine in diethyl ether. rSP-C was obtained as described above and dissolved in DMF/THF (50:50, volume/volume) and a 10- to 400-fold excess of 2-(palmitoyloxy) pyridine hydrochloride. The reaction mixture was incubated at 37° C. for 12–48 hours and then analyzed by HPLC. New peaks, more non-polar than SP-C, were collected and were found on mass spectrometric analysis to contain dipalmitoyl derivatives of SP-C.

Example 3
Mass spectrometry analysis of lung surfactant.

Results of mass spectral measurements for SP-C isolated from several species are summarized below. Mass measurements were all made at low resolution, by known methods, and the masses represent the protonated isotopic average mass. Mass accuracy is within 0.8 Da except in cases where the signal intensity is extremely low or resolution of the instrument count not separate overlapping peaks. When mixtures of peptides exist, e.g. N-terminal heterogeneity, all components may not be observed due to ion suppression phenomena.

In this example, palmityl-free SP-C was prepared for mass spectral analysis as follows: dry SP-C, 1–10 $\mu$g, was dissolved in 5 $\mu$l of 95% isopropanol, 5% trifluoroacetic acid and then vortexed for about 30 seconds. The sample was then concentrated on the mass spectrometer probe and 0.5 $\mu$l of m-nitrobenzoic acid was added to the sample probe.

The protocol for removal of palmityl thio esters from SP-C as used in this example was as follows: SP-C, 1–10 $\mu$g, was dissolved in 100 $\mu$l of freshly prepared cleavage buffer (which consists of 95% isopropanol and 5% 0.2M ammonium bicarbonate and is 0.2M in dithiothreitol). After the addition of cleavage buffer, the reaction tube was flushed with dry nitrogen and then sealed. Cleavage of thioesters was allowed to proceed for 5 hours at 37° C. Solvent was removed by lyophilization.

1. Canine SP-C

Canine SP-C was obtained and purified as described above. The observed MH+- 3797.9, and this mass matches the mass expected for the known amino acid sequence (3545.7) plus a palmityl group (presumably a thioester to cysteine) (238.1) plus a methyl ester (14.0) (presumably formed during prolonged storage of the SP-C in chloroform/methanol/HCl.

Treatment of Canine SP-C with DTT for 8 hours at 37° C. resulted in an observed MH+of 3559.0, corresponding to a total release of palmityl.

2, Bovine SP-C

Bovine SP-C was obtained and purified by known methods. The observed MH+- 4058.7, which matches the mass expected for the amino acid sequence (3582.7) plus 2 palmityl groups (476.2). Treatment of Bovine SP-C with DTT for 8 hour at 37° C. resulted in and observed MH+- 3581.9, corresponding to a total release of palmityl.

3. Human full-term amniotic SP-C

Human full-term amniotic SP-C was obtained and purified by known methods. The observed MH+matches that expected for the amino acid sequence (3965.2) plus two palmityl groups (476.2).

4. Human alveolar proteinosis SP-C

Human alveolar proteinosis SP-C was isolated and purified from lavage fluid according to known methods. The observed MH+- 4352.4, which matches that expected for the amino acid sequence (3818.0) plus 2 palmityl groups (476.2) plus isopropyl (42) plus Met-sulfoxide (16). Other peaks in the spectrum: MH+- 4114.3 (-238.1) represents the equivalent peptide less one palmityl group, MH+- 3876.2 (-2× 238.1) represents the equivalent peptide less two palmityl groups. The isopropyl ester could be formed during prolonged exposure to 95% isopropanol/5 mM HCl 5. Human recombinant SP-C Human recombinant SP-C was prepared by microbial expression according to known methods. The observed MH+- 3699.3, which matches that expected for the amino acid sequence (3686.8). Data shows this sample minus any palmityl groups.

Example 4
Imidazole Palmitoylation Methods

This example illustrates an alternative approach which is suitable for acylating the surfactant protein (here SP-C) chemically in vitro either before, during or after purification of the protein. The approach described in this disclosure involved acylation of homogenous rSP-C, but the reactions used to acylate the protein could be carried out prior to the last steps of purification, i.e., early in the purification scheme.

The palmitoylation reaction involves transfer of palmitic acid from the reagent N-palmitoylimidazole to the cysteine residues of SP-C. The reaction is catalyzed by excess imidazole. The acyl thioesters of SP-C were then purified by reverse phase HPLC.

The N-palmitoylimidazole was synthesized essentially as described by Cronan and Klages, PNAS 78:5440–5444 (1981). Palmitoyl chloride was added to twice the molar ratio of imidazole dissolved in benzene. The mixture was stirred for at least 3 hours and then filtered to remove the insoluble imidazolium chloride. The benzene was then removed by evaporation under vacuum. The residue was dissolved in ethyl acetate for subsequent recrystallization. The resulting N-palmitoylimidazole was used in subsequent reactions as the fatty acyl donor.

The initial acylation experiments were carried out in aqueous buffers using detergents to solubilize the SP-C. In these experiments, SP-C was dried under vacuum and redissolved in 10% Nonidet P-40 (Sigma). A 9-fold molar excess of palmitoylimidazole was added, and also enough imidazole to bring the concentration to approximately 500 mM. This 9-fold excess is an 18-fold molar excess with respect to the cysteines (2 cys/SP-C). The pH of the reaction was adjusted to 6.5. Dithiothreitol (DTT) (equimolar compared to SP-C) was also added. The reaction was allowed to proceed for fourteen hours with aliquots removed at 30 minutes and one hour for interim analysis.

Before analysis, aliquots from each time point were dried under vacuum and then solubilized in 35% isopropanol containing 5% 0.1 n HCl. These samples were then chromatographed over either Vydac C4 or C8 reverse phase HPLC columns. This technique allows resolution of the various species of palmitoylated SP-C. The conditions for the chromatography were as follows: buffer A—5 mM HCl, buffer B—100% isopropanol in 5 mM HCl, 40 minute gradient 35%–95% buffer B. The flow rate was 1 ml/min with the detector set at 228 rim.

The HPLC separation allows resolution of 4 separate peaks of acylated SP-C (data not shown). These peaks represent increasing numbers of palmitate groups (up to four) on SP-C. The SP-C containing four palmitate groups elutes last in the gradient (most hydrophobic) (peak 4) while the SP-C derivatized with only one palmitate elutes first (peak one). The results from this experiment can be summarized as follows: Aliquots taken early in the reaction (30 minutes and 1 hour) contained peak 1 and peak 2. These peaks contain SP-C with one and two palmitates respectively. With time (14 hours) peaks one and two decreased in magnitude while two additional peaks, 3 and 4, appeared. These peaks correspond to SP-C containing 3 and 4 palmitates. Approximately 75% of the palmitates on SP-C which elute in peak 1 and 2 are linked to cysteines. The remaining acylation is presumably to the amino groups on the n-terminal glycine and the epsilon amino group of lysine. These estimates are based on the ability of reducing agents to deacylate palmitates on cysteines but not on amino groups.

We also developed methods for cysteine acylation in nonaqueous solvent systems. In one method the SP-C was directly acylated with N-palmitoylimidazole in 95% isopropanol containing 5% 0.1 n HCl. The concentration of the acylating reagent was varied over a range of concentrations from 1 to 20 fold molar excess compared to SP-C (2–40 fold over the cysteine thiols). The time course of the reaction was also varied from 30 minutes to 16 hours. Again shorter reaction times favor the specific acylation of cysteine, while increasing times lead to the formation acyl-amino groups.

We claim:

1. A method for producing a lung surfactant composition which comprises:
   (a) expressing and recovering recombinantly produced SP-C surfactant protein having free sulfhydryl groups; and
   (b) treating the SP-C protein with an activated derivative of a fatty acid under conditions which result in the formation of fatty acid thioester groups at the cysteine residues of the SP-C protein; whereby
   (c) the product of step (b) exhibits a reduction in the tendency to aggregate when compared to the product of step (a).

2. (New) The method of claim 1, wherein the fatty acid is palmitic acid.

3. The method of claim 2, wherein the activated derivative of palmitic acid is selected from the group consisting of a phenyl ester of palmitic acid, a pyridine derivative of palmitic acid, palmitoyl chloride, N-palmitoylimidazole and palmitoyl CoA.

4. A method for producing a lung surfactant composition which comprises treating a synthetically produced SP-C protein having free sulfhydryl groups with an activated derivative of a fatty acid under conditions which result in the formation of fatty acid thioester groups at the cysteine residues of the SP-C protein to generate an aggregation-resistant synthetic SP-C protein.

5. The method of claim 4, wherein the fatty acid is palmitic acid.

6. The method of claim 5, wherein the activated derivative of palmitic acid is selected from the group consisting of a phenyl ester of palmitic acid, a pyridine derivative of palmitic acid, palmitoyl chloride, N-palmitoylimidazole and palmitoyl CoA.

* * * * *